United States Patent [19]

Hoogendoorn

[11] Patent Number: 4,871,532
[45] Date of Patent: Oct. 3, 1989

[54] MOUTH CARE PRODUCTS

[75] Inventor: Hendrik Hoogendoorn, Krimpen, Netherlands

[73] Assignee: Douwe Egberts Koninklijke Tabaksfabriek Koffiebranderijen-Theehandel N.V., Utrecht, Netherlands

[21] Appl. No.: 142,052

[22] Filed: Jan. 7, 1988

[30] Foreign Application Priority Data

Jan. 8, 1987 [NL] Netherlands ................... 8700025

[51] Int. Cl.$^4$ .................. A61K 7/16; A61K 7/22; A61K 7/28
[52] U.S. Cl. ...................................... 424/50; 424/54
[58] Field of Search .................... 424/49, 50, 54

[56] References Cited

U.S. PATENT DOCUMENTS

| | | | |
|---|---|---|---|
| 3,793,447 | 2/1974 | De Palma et al. | 424/54 |
| 4,022,880 | 5/1977 | Vinson et al. | 424/49 |
| 4,150,113 | 4/1979 | Hoogendoorn et al. | 424/50 |
| 4,152,418 | 5/1979 | Pader | 424/50 |
| 4,154,815 | 5/1979 | Pader | 424/50 |
| 4,178,362 | 12/1979 | Hoogendoorn et al. | 424/50 |
| 4,269,822 | 5/1981 | Pellico et al. | 424/50 |
| 4,537,764 | 8/1985 | Pellico et al. | 424/50 |
| 4,564,519 | 1/1986 | Pellico et al. | 424/50 |
| 4,578,265 | 3/1986 | Pellico et al. | 424/50 |

FOREIGN PATENT DOCUMENTS 1154427  6/1969  United Kingdom .

OTHER PUBLICATIONS

Harrap et al., CA. 100:151007a (1984) of Arch. Oral Biol. 29(2):87–91 (1984).

*Primary Examiner*—Shep K. Rose
*Attorney, Agent, or Firm*—Stevens, Davis, Miller & Mosher

[57] ABSTRACT

Mouth-care products containing an oxidoreductase and a combination of an 8-hydroxy-quinoline and a compound yielding zinc ions.

8 Claims, No Drawings

MOUTH CARE PRODUCTS

The invention relates to tooth-cleaning agents containing oxidoreductase, and to methods for the preparation thereof.

The Dutch Patent Specification 150,332 describes tooth-cleaning agents which, in addition to the ingredients which are usual for said agents, also contain an enzyme which yields hydrogen peroxide on breaking down a substrate. Depending on the nature of such an oxidoreductase, the relevant substrate and/or another enzyme which can convert compounds present in the mouth or on the tooth surface into a substrate for the oxidoreductase used are also added to the tooth cleaning agent.

Use is made of such an enzyme system yielding hydrogen peroxide to achieve normalization of the mouth flora via the lactoperoxidase (saliva peroxidase) present in the saliva and the hypothiocyanite additionally formed, as a result of which the formation of harmful acids is prevented.

According to this principle, the acid-forming bacteria are not killed but a temporary inactivation takes place of the enzymes which occur in said bacteria and which are responsible for the acid formation.

It has been found, however, that under certain circumstances said inactivation does not take place, or takes place to a reduced extent, which depends, inter alia, on the nature of the food and the frequency at which it is consumed.

A large number of articles have previously proposed adding bactericidal substances to tooth-cleaning agents in order to kill the acid-forming bacteria. The great disadvantage thereof is that this may lead to the production of resistant strains and the growth of undesirable micro-organisms.

If bacteria are killed but not removed, autolysis of the dead cells will also occur as a result of which the surviving cells have additional nutrient substances at their disposal which is the very thing which promotes harmful acid formation.

Surprisingly, it has now been found that the use of a combination of zinc ions and an 8-hydroxyquinoline in concentrations in which each of the two components separately and also in combination have no bactericidal action increases the inactivation of the acid-forming bacteria in an oxidoreductase-containing tooth-cleaning agent, even under the unfavourable conditions outlined above.

The invention therefore relates to oxidoreductase-containing tooth-cleaning agents, optionally containing a substrate for such an oxidoreductase and/or an enzyme which can yield said substrate, by adding thereto a combination of an 8-hydroxyquinoline and a compound yielding zinc ions, and to methods for the preparation thereof.

As stated, the combination of zinc ions and an 8-hydroxyquinoline is used in such concentrations that neither the components separately nor the combination has a bactericidal action.

The 8-hydroxyquinoline concerned is used in a concentration which is between $5 \times 10^{-5}$ and $10^{-1}$ % by weight of the tooth-cleaning agent, and zinc (in ionic form) in a concentration which is between $10^{-5}$ and $10^{-1}$ % by weight.

It has been found that the use of the 8-hydroxyquinoline concerned in a concentration of $5 \times 10^{-4}$ to $10^{-3}$ % by weight and of zinc (ions) in a concentration of $10^{-4}$ to $5 \times 10^{-3}$ has an especially effective action.

The zinc compound to be used may be any pharmaceutically acceptable, water-soluble zinc compound derived from inorganic or organic acids such as zinc sulphate, zinc citrate, zinc gluconate, zinc acetate etc., but usually the zinc salt of the 8-hydroxyquinoline is used.

The 8-hydroxyquinoline to be added may be 8-hydroxyquinoline itself, or derivatives thereof, such as substituted derivatives, esters, for example the acetate or sulphate, or acid addition salts thereof.

Of the substituted derivatives, consideration is preferably given to the halogenated derivatives, such as the 5-halo, 7-halo, and 5,7-dihalo derivatives.

The combination of zinc ions and an 8-hydroxyquinoline described above is added to an oxidoreductase-containing tooth-cleaning agent.

Said oxidoreductase may be any oxidoreductase yielding hydrogen peroxide, such as lactate oxidase, glucose oxidase, pyruvate oxidase, xanthine oxidase etc.

The quantity of oxidoreductase is usually between 0.01 and 500 units per gram/millilitre of the tooth-cleaning agent.

A unit of enzyme is understood to mean the quantity which breaks down 1 $\mu$mol of substrate per minute at 30° C. and under standard conditions.

One or more other enzymes, preferably hydrolases, such as carabohydrases and proteases, can also be added in addition.

Preferably glucose oxidase is used as oxidoreductase, optionally in the presence of amyloglucosidase as hydrolase, and/or glucose as substrate.

The effect of the combination according to the invention was manifestly demonstrated by means of human saliva, the mouth flora of which has been stimulated, i.e. has acquired an increased resistance to inactivation, by treatment with glutathion.

Said saliva was introduced into a number of small containers, 1% of fructose being added, and the acid formation was measured by titration at a certain pH and temperature after adding a substance to be determined.

From the table below it is then evident that adding one of the components comprising zinc, 8-hydroxyquinoline line and glucose oxidase, and combinations of two of the said components does not slow down the acid formation, while the total combination does in fact do this.

TABLE

| | |
|---|---|
| 1. ZnSO$_4$.7 H$_2$O $10^{-3}$ % by weight | acid formation |
| 2. 8-hydroxyquinoline $10^{-3}$ % by weight | acid formation |
| 3. ZnSO$_4$.7 H$_2$O + 8-hydroxyquinoline combination of 1 and 2 | acid formation |
| 4. Glucose oxidase (see Dutch Patent Specification 150,332) | acid formation |
| 5. Combination of 1 + 4 | acid formation |
| 6. Combination of 2 + 4 | acid formation |
| 7. Combination 3 + 4 | no acid formation |

The tooth-cleaning agents according to the invention can be converted to various forms, such as to the form of a toothpaste, mouthwash, tablet, chewing gum or other conventional form.

In addition to the components according to the invention, said tooth-cleaning agents may also contain the other usual excipients, such as abrasing and polishing agents, thickening agents, colourants, sweetening agents, fluorine compounds, and the like.

The invention is explained in more detail by reference to the following compositions, without, of course, being restricted thereto.

Example 1
Toothpaste

| | |
|---|---|
| Sorbitol | 22% (by weight) |
| Silica | 22% |
| Ethoxylated fatty alcohol | 3% |
| Carragheen | 1.5% |
| Sodium benzoate | 0.1% |
| Flavouring | 0.6% |
| Sodium saccharinate | 0.1% |
| Amyloglucosidase | 18 U/g |
| Glucose oxidase | 6 U/g |
| Zinc sulphate 7 $H_2O$ | $10^{-3}$% |
| 8-hydroxyquinoline | $10^{-3}$% |
| Water | to 100% |

Example 2
Toothpaste

| | |
|---|---|
| Glycerol | 15% (by weight) |
| Aluminium oxide hydrate | 35% |
| Ethoxylated fatty alcohol | 2.5% |
| Carragheen | 2% |
| P.H.B. esters | 0.15% |
| Flavouring | 1.2% |
| Sodium fluoride | 0.24% |
| Mutanase | 15 U/g |
| Glucose oxidase | 8 U/g |
| Invertase | 5 U/g |
| Zinc gluconate | $8 \times 10^{-4}$% |
| 5-chloro-8-hydroxyquinoline | $10^{-3}$% |
| Water | to 100% |

Example 3
Mouthwash

| | |
|---|---|
| Glycerol | 15% (by weight) |
| Xylitol | 15% |
| Flavouring | 0.05% |
| Tween 80 | 2% |
| Propyl p-hydroxybenzoate | 0.1% |
| Potassium thiocyanate | 0.02% |
| Sodium citrate | 0.2% |
| Amyloglucosidase | 4 U/g |
| Glucose oxidase | 1 U/g |
| Zinc citrate | $2 \times 10^{-4}$% |
| 8-hydroxyquinoline sulphate | $10^{-4}$% |
| Water | to 100% |

Example 4
Lozenge

| | |
|---|---|
| Sorbitol | 1500 mg |
| Encapsulated flavouring | 10 |
| Sodium stearate | 10 |
| Phosphate buffer pH = 7 | 50 |
| P.V.P. | 20 |
| Zinc 8-hydroxyquinolate | 0.16 mg |
| Glucose oxidase | 50 U |
| Amyloglucosidase | 100 U |

Example 5
Effervescent tablet

| | |
|---|---|
| $NaHCO_3$ | 40 mg |

-continued

| | |
|---|---|
| Citric acid | 20 |
| P.V.P. | 2 |
| Sorbitol | 24 |
| Encapsulated flavouring | 2 |
| Glucose | 2 |
| Glucose oxidase | 10 U |
| Lactoperoxidase | 100 U |
| Potassium thiocyanate | 1 |
| Zinc 8-hydroxyquinolate | 0.3 mg |
| Dissolve in: | 15 ml of water. |

I claim:

1. An oxidoreductase-containing tooth-cleaning agent comprising an oxidoreductase yielding hydrogen peroxide upon breaking down a substrate in a quantity of between 0.01 and 500 units per gram/milliliter of tooth cleaning agent, each unit of enzyme being the quantity which breaks down 1 $\mu$-mol of substrate per minute at 30° C. and under standard conditions; a 8-hydroxyquinoline, ester thereof or acid addition salt thereof; and a water-soluble compound yielding Zn ions, said 8-hydroxyquinoline, ester and acid addition salt thereof being present in a concentration of between $5 \times 10^{-5}$ and $10^{-1}$ % by weight and said zinc in ionic form being present in a concentration of between $10^{-5}$ and $10^{-1}$ % by weight and said zinc in ionic form being present in a concentration of between $10^{-5}$ and $10^1$ % by weight.

2. The tooth-cleaning agent according to claim 1, wherein said 8-hydroxyquinoline, ester thereof or acid addition salt thereof is substituted by at least one halogen.

3. The tooth-cleaning agent of claim 1, wherein the water-soluble compound yielding Zn ions is a zinc salt of 8-hydroxyquinoline.

4. The tooth-cleaning agent of claim 2, wherein the water-soluble compound yielding Zn ions is a zinc salt of 8-hydroxyquinoline.

5. The tooth-cleaning agent according to claim 1, wherein the 8-hydroxyquinoline, ester thereof or acid addition salt thereof is present in a concentration of between $5 \times 10^{-4}$ and $10^{-3}$ % by weight and said zinc in ionic form is present in a concentration of between $10^{-4}$ and $5 \times 10^{-3}$ % by weight.

6. The tooth-cleaning agent according to claim 2, wherein the 8-hydroxyquinoline, ester thereof or acid addition salt thereof is present in a concentration of between $5 \times 10^{-4}$ and $10^{-3}$ % by weight and said zinc in ionic form is present in a concentration of between $10^{-4}$ and $5 \times 10^{-3}$ % by weight.

7. The tooth-cleaning agent according to claim 3, wherein the 8-hydroxyquinoline, ester thereof or acid addition salt thereof is present in a concentration of between $5 \times 10^{-4}$ and $10^{-3}$ % and said zinc in ionic form is present in a concentration of between $10^{-4}$ and $5 \times 10^{-3}$ % by weight.

8. The tooth-cleaning agent according to claim 4, wherein the 8-hydroxyquinoline, ester thereof or acid addition salt thereof is present in a concentration of between $5 \times 10^{-4}$ and $10^{-3}$ % by weight and said zinc in ionic form is present in a concentration of between $10^{-4}$ and $5 \times 10^{-3}$ % by weight.

* * * * *